US011395725B2

(12) United States Patent
Jones et al.

(10) Patent No.: US 11,395,725 B2
(45) Date of Patent: Jul. 26, 2022

(54) AORTOILIAC IMPLANT AND PROCESSING AND USES THEREOF

(71) Applicant: LifeNet Health, Virginia Beach, VA (US)

(72) Inventors: Alyce Linthurst Jones, Virginia Beach, VA (US); Jason B. Schulte, Virginia Beach, VA (US); Eric Moore, Virginia Beach, VA (US); Perry L. Lange, Virginia Beach, VA (US); Rex Nagao, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 102 days.

(21) Appl. No.: 16/329,898

(22) PCT Filed: Sep. 19, 2018

(86) PCT No.: PCT/US2018/051800
§ 371 (c)(1),
(2) Date: Mar. 1, 2019

(87) PCT Pub. No.: WO2019/060445
PCT Pub. Date: Mar. 28, 2019

(65) Prior Publication Data
US 2021/0330444 A1 Oct. 28, 2021

Related U.S. Application Data

(60) Provisional application No. 62/560,463, filed on Sep. 19, 2017.

(51) Int. Cl.
*A61F 2/06* (2013.01)
(52) U.S. Cl.
CPC ........ *A61F 2/064* (2013.01); *A61F 2002/065* (2013.01); *A61F 2240/008* (2013.01)

(58) Field of Classification Search
CPC ................ A61F 2/064; A61F 2002/065; A61F 2240/008
See application file for complete search history.

(56) References Cited

U.S. PATENT DOCUMENTS

| 5,755,659 A | 5/1998 | Zurbrügg |
| 6,293,970 B1 | 9/2001 | Wolfinbarger et al. |

(Continued)

FOREIGN PATENT DOCUMENTS

WO 2006054968 A1 5/2006

OTHER PUBLICATIONS

International Preliminary Report on Patentability and Written Opinion for International Application No. PCT/US2018/051800, dated Mar. 24, 2020, 6 pages.

(Continued)

*Primary Examiner* — Jason-Dennis N Stewart
(74) *Attorney, Agent, or Firm* — RatnerPrestia

(57) ABSTRACT

The present invention provides a package comprising an aortoiliac artery graft and a record of a measured pressurized diameter of the aortoiliac artery graft, which measurement has been determined ex vivo under a pressure. A method of processing an aortoiliac artery graft is also provided. The processing method comprises subjecting an aortoiliac artery to a pressure ex vivo, and determining a measured pressurized diameter of the aortoiliac artery under the pressure. A method of treating abdominal aortic aneurysm, infected aortoiliac endograft or a traumatically damaged abdominal aorta or an iliac artery in a patient is further provided. The treatment method comprises anastomosing a processed aortoiliac artery graft with an aorta of the patient on the proximal end and the iliac or femoral arteries on the distal (Continued)

end, wherein a measured pressurized diameter of the processed aortoiliac artery graft has been determined ex vivo under a pressure.

20 Claims, 15 Drawing Sheets

(56) References Cited

U.S. PATENT DOCUMENTS

| | | |
|---|---|---|
| 6,517,572 B2 | 2/2003 | Kugler et al. |
| 6,544,289 B2 | 4/2003 | Wolfinbarger et al. |
| 6,569,200 B2 | 5/2003 | Wolfinbarger et al. |
| 7,063,726 B2 | 6/2006 | Crouch et al. |
| 7,775,965 B2 | 8/2010 | McFetridge |
| 9,517,069 B2 | 12/2016 | Zilla et al. |
| 2003/0097040 A1 | 5/2003 | Clerin et al. |
| 2003/0110830 A1 | 6/2003 | Dehdashtian et al. |
| 2007/0260109 A1 | 11/2007 | Squillace |
| 2010/0030340 A1 | 2/2010 | Wolfinbarger et al. |
| 2011/0015757 A1 | 1/2011 | Wolfinbarger et al. |
| 2013/0218294 A1 | 8/2013 | Wolfinbarger et al. |
| 2014/0180437 A1 | 6/2014 | Wolfinbarger et al. |
| 2014/0379010 A1 | 12/2014 | Zilla et al. |

OTHER PUBLICATIONS

"Aortoiliac Allograft Outer Diameter Measurement: Why Pressurization Matters", LifeNet Health, 2 pages (2017).
"CryoArtery", CryoLife, 20 pages (2016).
International Search Report and Written Opinion for International Application No. PCT/US2018/051800, by Lee W. Young dated Jan. 30, 2019 (6 pages).
Extended European Search Report for European Application No. 18 858 524.4, dated Jun. 2, 2021, 9 pages.
Rieu, R., et al., "In Vitro Study of a Physiological Type Flow in a Bifurcated Vascular Prothesis," Journal of Biomechanics, Pergamon Press, vol. 24(10), Jan. 1, 1991, pp. 923-933, XP026275324.

FIG. 9A

| Product Dimensions | |
|---|---|
| Label Description | 1. CRYO. AORTOILIAC ARTERY |
| | 2. CRYO. DISTAL AORTOILIAC ARTERY |
| | 3. CRYO. ABDOMINAL AORTA |
| Size / Amount | Diameter (mm): Aorta, inner diameter (ID), flaccid, HV sizer and outer diameter (OD), distended (under ~125 mmHg pressure), ruler.<br>Length (cm) = Aorta and iliac arteries, flaccid, ruler. |
| Aorta Diameters | Aorta Flaccid Diameter (AFD): Measure, inner diameter (mm) of a flaccid aorta with a HV sizer. To measure, wet the sizer and slide it into the aorta. The appropriate dimension sizer should slide into the artery without any pressure inside the vessel and without leaving gaps or dilation of the arterial wall. |
| | Aorta Distended Diameter (ADD): Use the pressure relief valve assembly to inflate the graft with isotonic solution. Use a ruler to measure the outer diameter of the distended graft at the approximate location where the flaccid diameter measurement was taken. |
| Aorta Length (AL) | Measure, in cm, flaccid aorta from the proximal end of the aorta to above the approximate origin of the common right and left iliac arteries (see attached photos). |
| Iliac Arteries, Right (RIA) and Left (LIA) | Measure, in cm, flaccid iliac arteries from the origin at the aorta to distal end of the right and left iliac artery (see attached photos). |
| Celiac Trunk | Measure, in cm, under flaccid conditions. Minimum acceptable length is ≥ 0.5 cm when measured from the aorta distally to the end of the artery. |
| Superior Mesenteric Artery (SMA) | |
| Renal Right & Left | |
| Total Flaccid Length (TFL) | Measure, in cm, under flaccid conditions, from the proximal end of the aorta to the distal end of the shortest iliac artery. |
| Code | Tolerance |
| Aortoiliac Artery (AI) | Diameter (mm): Aorta, flaccid; ≥10 mm (Table 1).<br>Length (cm): Aorta, flaccid; 1.0 cm increments (12 cm max length, 6 cm min length). Iliac arteries, flaccid; 1.0 cm increments (≥ 4 cm minimum). Major arterial branches (celiac, renal and mesenteric arteries), flaccid; minimum ≥ 0.5 cm. |
| Distal Aortoiliac Artery (DAI) | Diameter: Aorta, flaccid; ≥ 10 mm (Table 1).<br>Length: Aorta (infrarenal), flaccid; 1.0 cm increments (12 cm maximum length, 6 cm minimum). Iliac arteries, flaccid; 1.0 cm increments (≥ 4 cm minimum). |
| Abdominal Aorta (ABA) | Diameter: Aorta diameter, flaccid; ≥ 10 mm (Table 1).<br>Length: Aorta (infrarenal), flaccid; 1.0 cm increments (12 cm maximum length, 6 cm minimum). Iliac arteries, flaccid; 1.0 cm increments (≥ 0.5 cm minimum). |

| Table 1: Aorta Diameter Tolerances and Codes | | |
|---|---|---|
| Flaccid (ID) | Distended (OD) | |
| Hegar (mm) | Mimimum (mm) | Maximum (mm) |
| 10 | 14 | 21 |
| 11 | 15 | 23 |
| 12 | 16 | 25 |
| 13 | 17 | 26 |
| 14 | 18 | 28 |
| 15 | 20 | 28 |
| 16 | 21 | 28 |
| 17 | 22 | 28 |
| 18 | 23 | 28 |
| 19 | 24 | 28 |
| 20 | 25 | 28 |

ANTERIOR VIEW

POSTERIOR VIEW

DISTAL AORTOILIAC ARTERY (DAI): MEASUREMENT KEY

[AFD] = AORTA, flaccid external diameter (mm)
[ADD] = AORTA, distended (~125 mmHg) external diameter (mm)
[AL] = AORTA, length (cm)
[LIA] = LEFT ILIAC ARTERY, length (cm)
[RIA] = RIGHT ILIAC ARTERY, length (cm)
[TFL] = TOTAL FLACCID LENGTH, flaccid length of the aorta and the shortest iliac artery (cm)

ABDOMINAL AORTA ARTERY (ABA): MEASUREMENT KEY

[AFD] = AORTA, flaccid external diameter (mm)
[ADD] = AORTA, distended (~ 125 mmHg) external diameter (mm)
[AL] = AORTA, length (cm)
[LIA] = LEFT ILIAC ARTERY, flaccid length (cm)
[RIA] = RIGHT ILIAC ARTERY, flaccid length (cm)
[TFL] = TOTAL FLACCID LENGTH, flaccid length of the aorta and the shortest iliac artery (cm)

FIG. 10A

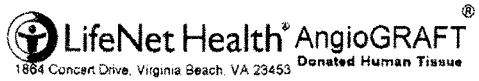

LifeNet Health® AngioGRAFT®
1864 Concert Drive, Virginia Beach, VA 23453  Donated Human Tissue
CRYO. DISTAL AORTOILIAC ARTERY
DAI
Size: FD=10 MM, DD=17 MM
ID: 1716241-0001
Exp. Date: 2022-06-19
FROZEN HUMAN TISSUE - Single Patient Use Only
Store at liquid nitrogen vapor phase temperature (-120C or below)
UDI:            (01)00889858605977(17)220619(21)1716241-0001
Caution: See package insert for precautionary and preparation information.
For LNH Internal Use Only: DAI1017                FMT-0026

LifeNet Health® AngioGRAFT®
1864 Concert Drive, Virginia Beach, VA 23453  Donated Human Tissue
CRYO. AORTOILIAC ARTERY
AI
Size: FD=12 MM, DD=21 MM
ID: 1716225-0009
Exp. Date: 2022-06-19
FROZEN HUMAN TISSUE - Single Patient Use Only
Store at liquid nitrogen vapor phase temperature (-120C or below)
UDI:            (01)00889858604420(17)220619(21)1716225-0009
Caution: See package insert for precautionary and preparation information.
For LNH Internal Use Only: AI1221                FMT-0026

CRYO. DISTAL AORTOILIAC ARTERY
Code: DAI
FD=10 MM, DD=17 MM
ID: 1716241-0001
Exp. Date: 2022-06-19
UDI:     (01)00889858605977(17)220619(21)1716241-0001

CRYO. AORTOILIAC ARTERY
Code: AI
FD=12 MM, DD=21 MM
ID: 1716225-0009
Exp. Date: 2022-06-19
UDI:     (01)00889858604420(17)220619(21)1716225-0009

ID: 1716241-0001
DAI - CRYO. DISTAL AORTOILIAC ARTERY
Size: FD=10 MM, DD=17 MM
Exp. Date: 2022-06-19
UDI:     (01)00889858605977(17)220619(21)1716241-0001
Distributed by LifeNet Health®

ID: 1716225-0009
AI - CRYO. AORTOILIAC ARTERY
Size: FD=12 MM, DD=21 MM
Exp. Date: 2022-06-19
UDI:     (01)00889858604420(17)220619(21)1716225-0009
Distributed by LifeNet Health®

ID: 1716241-0001
DAI - CRYO. DISTAL AORTOILIAC ARTERY
Size: FD=10 MM, DD=17 MM
Exp. Date: 2022-06-19
UDI:     (01)00889858605977(17)220619(21)1716241-0001
Distributed by LifeNet Health®

ID: 1716225-0009
AI - CRYO. AORTOILIAC ARTERY
Size: FD=12 MM, DD=21 MM
Exp. Date: 2022-06-19
UDI:     (01)00889858604420(17)220619(21)1716225-0009
Distributed by LifeNet Health®

ID: 1716241-0001
DAI - CRYO. DISTAL AORTOILIAC ARTERY
Size: FD=10 MM, DD=17 MM
Exp. Date: 2022-06-19
UDI:     (01)00889858605977(17)220619(21)1716241-0001
Distributed by LifeNet Health®

ID: 1716225-0009
AI - CRYO. AORTOILIAC ARTERY
Size: FD=12 MM, DD=21 MM
Exp. Date: 2022-06-19
UDI:     (01)00889858604420(17)220619(21)1716225-0009
Distributed by LifeNet Health®

ID: 1716241-0001
DAI - CRYO. DISTAL AORTOILIAC ARTERY
Size: FD=10 MM, DD=17 MM
Exp. Date: 2022-06-19
UDI:     (01)00889858605977(17)220619(21)1716241-0001
Distributed by LifeNet Health®

ID: 1716225-0009
AI - CRYO. AORTOILIAC ARTERY
Size: FD=12 MM, DD=21 MM
Exp. Date: 2022-06-19
UDI:     (01)00889858604420(17)220619(21)1716225-0009
Distributed by LifeNet Health®

ID: 1716241-0001
DAI - CRYO. DISTAL AORTOILIAC ARTERY
Size: FD=10 MM, DD=17 MM
Exp. Date: 2022-06-19
UDI:     (01)00889858605977(17)220619(21)1716241-0001
Distributed by LifeNet Health®

ID: 1716225-0009
AI - CRYO. AORTOILIAC ARTERY
Size: FD=12 MM, DD=21 MM
Exp. Date: 2022-06-19
UDI:     (01)00889858604420(17)220619(21)1716225-0009
Distributed by LifeNet Health®

ID: 1716241-0001
DAI - CRYO. DISTAL AORTOILIAC ARTERY
Size: FD=10 MM, DD=17 MM
Exp. Date: 2022-06-19
UDI:     (01)00889858605977(17)220619(21)1716241-0001
Distributed by LifeNet Health®

ID: 1716225-0009
AI - CRYO. AORTOILIAC ARTERY
Size: FD=12 MM, DD=21 MM
Exp. Date: 2022-06-19
UDI:     (01)00889858604420(17)220619(21)1716225-0009
Distributed by LifeNet Health®

AORTOILIAC IMPLANT AND PROCESSING AND USES THEREOF

CROSS-REFERENCE TO RELATED APPLICATIONS

This application is a U.S. National Phase Application of International Application No. PCT/US2018/051800, filed on Sep. 19, 2018, which claims the benefit of U.S. Provisional Application No. 62/560,463, filed Sep. 19, 2017, the contents of which are incorporated herein by reference in their entireties for all purposes.

FIELD OF THE INVENTION

The invention relates generally to aortoiliac artery (AI) grafts and processing and uses thereof.

BACKGROUND OF THE INVENTION

Although widely used for treatment of abdominal aortic aneurysm (AAA), synthetic vascular grafts often cause primary infection and aortic graft-enteric erosion and present a serious risk of mortality and morbidity (limb loss, recurrent infections and paralysis). Cryopreserved, decellularized and devitalized aortoiliac artery (AI) grafts are an ideal solution to replace infected synthetic grafts. Given the severity of surgical cases, clinicians must intervene quickly or the patient will likely succumb to sepsis. Matching the size and configuration of an aortoiliac artery (AI) graft with a patient's aorta in need of surgery is critical to a successful surgery and long-term outcomes. A wide variation exists in graft inner diameter (ID) and the resultant outer diameter (OD) under arterial pressures vs in the flaccid or unpressurized state from person to person, or donor to donor. In other words, a flaccid inner diameter will produce a variety of pressurized inner/outer dimeters, in a donor dependent fashion, when subjected to arterial pressures. An unexpected relationship between flaccid and pressurized diameters is that smaller diameter aortas are more distensible than their larger diameter counterparts measured at the same anatomical location immediately distal to the diaphragm. Therefore, using a "one size fits all" approach to develop a single multiplier value to apply to a flaccid outer or inner diameter to predict the required post-implant pressurized outer/inner diameter is not conducive to a satisfactory surgical outcome because of this unexpected finding. Diameter variability may lead to patient mismatch with AI grafts leading to early failure as a result of non-laminar blood flow or extended surgical times to surgically manipulate the receiving aorta and AI to achieve the best possible match between them thus increasing the risk of adverse events and increased healthcare costs. As such, it is highly desirable to have accurate measurements of pressurized AI graft ID or OD taken at time of graft processing for better patient matches. Such accurate ID or OD measurements would improve and shorten pre-operative planning; minimize risk during surgery by eliminating the extra time needed to fashion an otherwise ill-fitting graft to the anastomotic site; and likely result in more favorable outcomes since a size-matched graft will avoid hemodynamic disruptions which occur with abrupt changes in the diameter of the vascular conduit due to mismatched grafts. None of the allograft AI grafts currently commercially available provides pressurized ID or OD measurements. Thus, there is a need for aortoiliac artery (AI) grafts of multiple configurations and accurate pressurized diameter measurements to match patients' aorta for use in clinical cases where aortic reconstruction, repair, or replacement is necessary.

SUMMARY OF THE INVENTION

The present invention relates to an aortoiliac artery graft with a measured pressurized diameter, and processing and uses thereof.

A package comprising an aortoiliac artery graft and a first record is provided. The first record provides a measured pressurized diameter of the aortoiliac artery graft, and the measured pressurized diameter has been determined ex vivo under a pressure. The measured pressurized diameter may be a measured pressurized outer diameter of the aortoiliac artery graft. The measured pressurized diameter may be a measured pressurized inner diameter of the aortoiliac artery graft. The pressure may be in a range of 120-140 mmHg.

The package may further comprise a second record. The second record may provide a measured unpressurized diameter of the aortoiliac artery graft, and the unpressurized diameter may have been determined ex vivo. The measured unpressurized diameter may be a measured unpressurized outer diameter of the aortoiliac artery graft. The measured unpressurized diameter may be a measured unpressurized inner diameter of the aortoiliac artery graft.

In the package, the aortoiliac artery graft may comprise a full aortoiliac artery, an abdominal aorta distal to renal arteries inclusive of iliac arteries to an iliofemoral junction, or an abdominal aorta distal of renal arteries and inclusive of at least 1 cm of an iliac artery.

The aortoiliac artery may comprise a distal aorta and iliacs without renal arteries. The aortoiliac graft may comprise an aorta distal of a diaphragm to iliofemoral junction. The aortoiliac artery graft may comprise an aorta artery and one iliac artery. The aortoiliac artery graft may comprise an aorta artery and two iliac arteries.

The aortoiliac artery graft may further comprise at least one renal artery. The aortoiliac artery graft may further comprise two renal arteries. The aortoiliac artery graft may further comprise an iliofemoral junction.

The aortoiliac artery graft may be decellularized and/or devitalized. The aortoiliac artery graft may be plasticized using a solution comprising glycerol at a concentration in the range of 35-60% by volume.

A method of processing an aortoiliac artery graft is also provided. The processing method comprises subjecting an aortoiliac artery to a pressure ex vivo, and determining a measured pressurized diameter of the aortoiliac artery under the pressure. As a result, a processed aortoiliac artery graft is obtained.

The pressure applied may be controlled by using a pressure relief valve or a calibrated syringe. The measured pressurized diameter may be determined by using a tool selected from the group consisting of a ruler, a caliper, an umbilical tape, a laser micrometer and ultrasound. The pressurized diameter may be a measured pressurized outer diameter of the aortoiliac artery. The pressurized diameter may be a measured pressurized inner diameter of the aortoiliac artery.

The processing method may further comprise determining a measured unpressurized diameter of the aortoiliac artery. The measured unpressurized diameter may be a measured unpressurized outer diameter of the aortoiliac artery. The measured unpressurized diameter may be a measured unpressurized inner diameter of the aortoiliac artery.

The processing method may further comprise releasing the pressure from the aortoiliac artery. The processing method may further comprise isolating the aortoiliac artery from a donor.

According to the processing method, the aortoiliac artery graft may be decellularized and/or devitalized. The aortoiliac artery graft may be plasticized using a solution comprising glycerol at a concentration in the range of 35-60% by volume.

According to each processing method, a processed aortoiliac artery graft is prepared.

A method of treating abdominal aortic aneurysm, infected aortoiliac endograft or a traumatically damaged abdominal aorta or an iliac artery in a patient is further provided. The treatment method comprises anastomosing a processed aortoiliac artery graft with an aorta of the patient on the proximal end and the iliac or femoral arteries on the distal end. A measured pressurized diameter of the processed aortoiliac artery graft has been determined ex vivo under a pressure.

The treatment method may further comprise matching the measured pressurized diameter of the processed aortoiliac artery graft with a diameter measurement of the aorta of the patient before the anastomosing step.

According to the treatment method, the measured pressurized diameter of the processed aortoiliac artery graft may be within 90-110% of the diameter measurement of the aorta of the patient. The measured pressurized diameter of the processed aortoiliac artery graft may be a measured pressurized outer diameter of the processed aortoiliac artery graft, the diameter measurement of the aorta is an inner diameter measurement of the aorta, and the measured pressurized outer diameter of the processed aortoiliac artery graft is within 97-103% of the inner diameter measurement of the aorta. The processed aortoiliac artery graft may be prepared according to the method of the present invention.

BRIEF DESCRIPTION OF THE DRAWINGS

FIGS. 9A-F show different configurations of AI grafts.

FIGS. 10A-B shows exemplary labels.

DETAILED DESCRIPTION OF THE INVENTION

Figure 1:
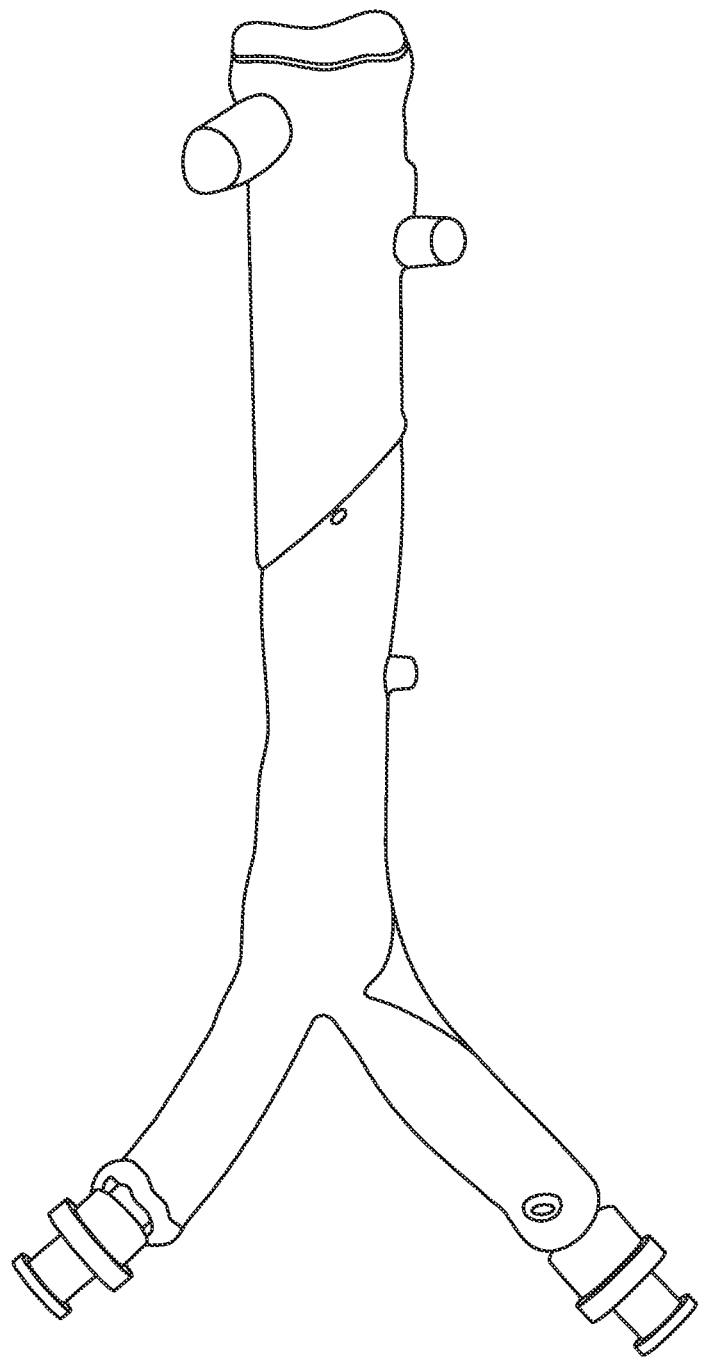
FIG. 1 shows a processed human aortoiliac artery (AI) graft including figure-of-eight mattress ligations. The graft is shown with male barbed Luer attachments used to cannulate both the iliac branches for connection to the pressurization testing model.
Figure 2:
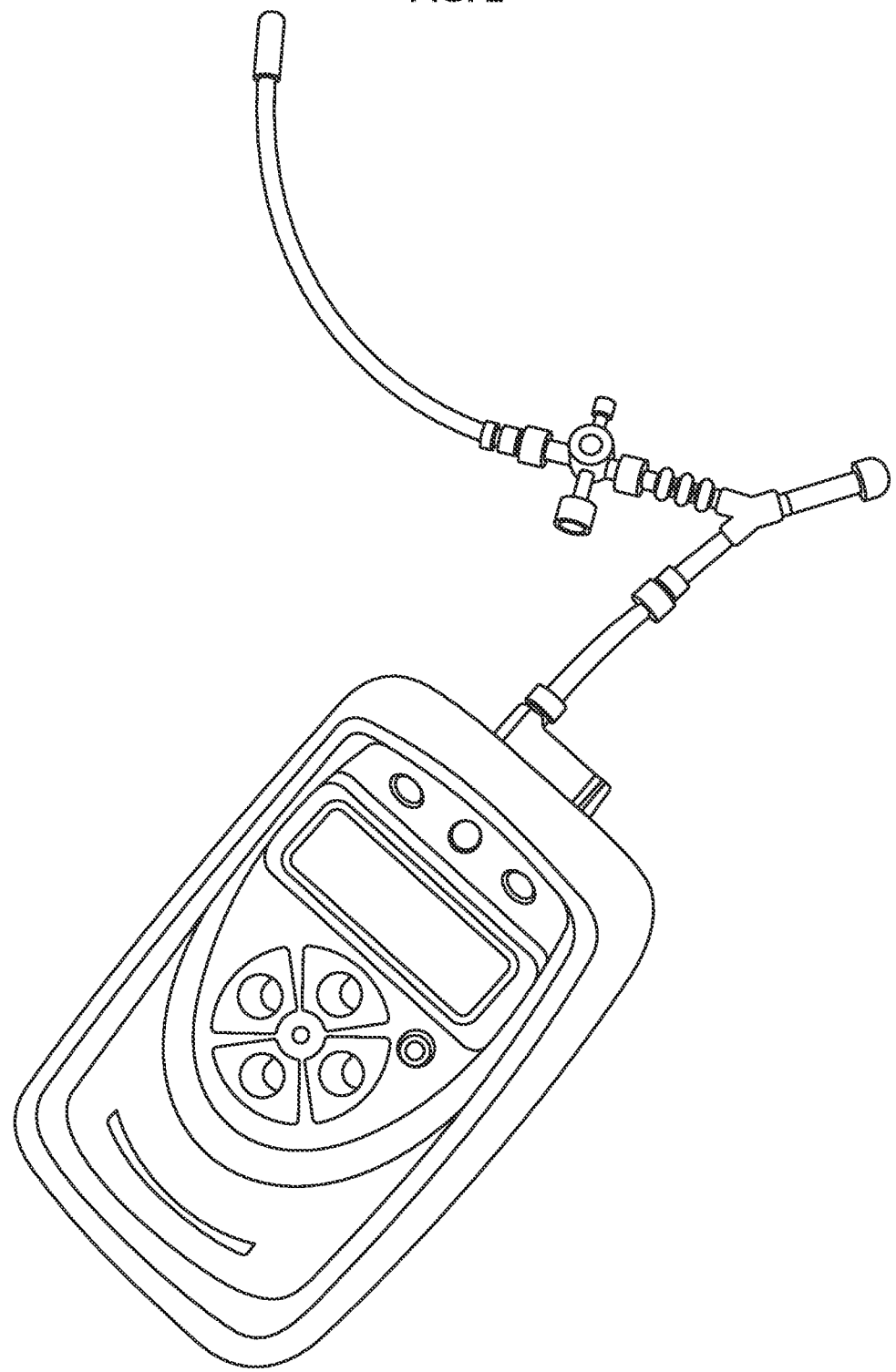
FIG. 2 shows a digital manometer and other components of a pressurization testing setup, including a tubing y-connector, a 3-way stopcock, and a drain tube.
Figure 3:
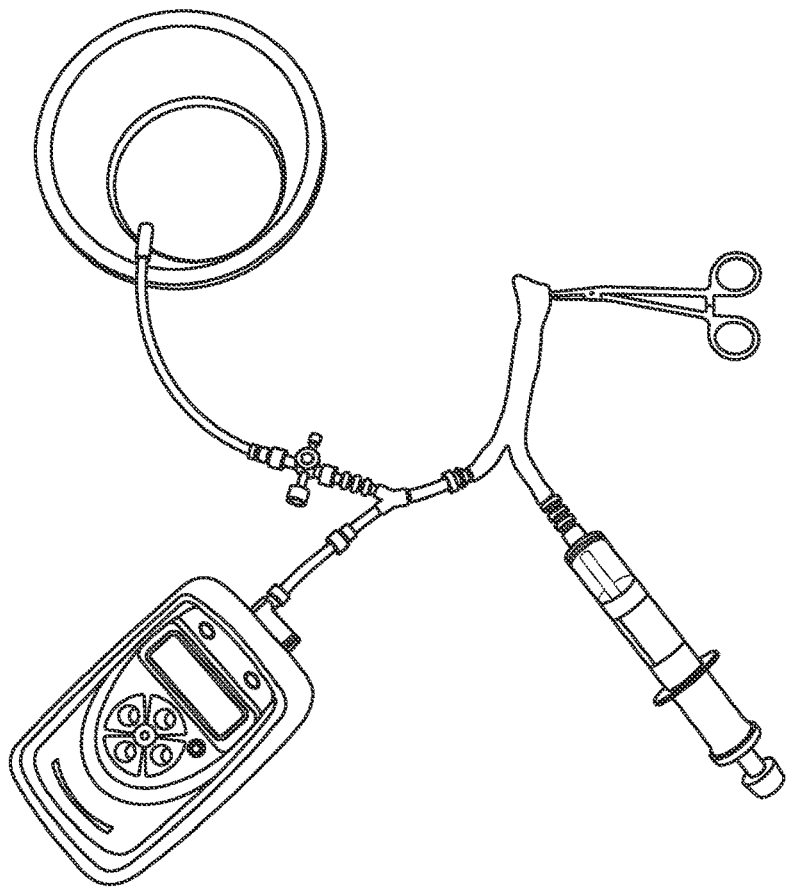
FIG. 3 shows a full pressurization testing assembly for an AI model.
Figure 4:
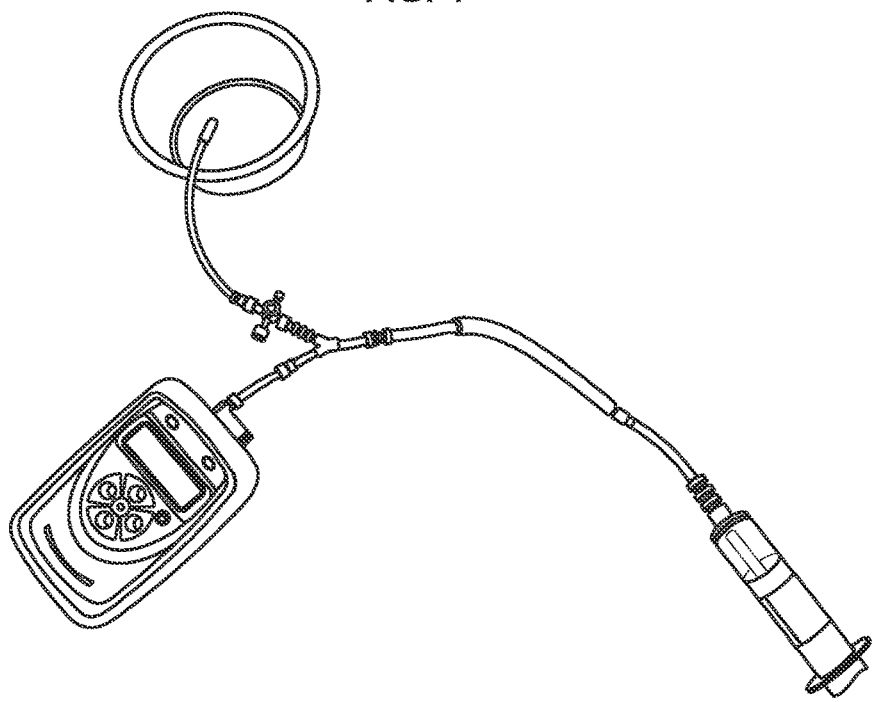
FIG. 4 shows a full pressurization testing assembly for a synthetic elastomer vessel model.
Figure 5:
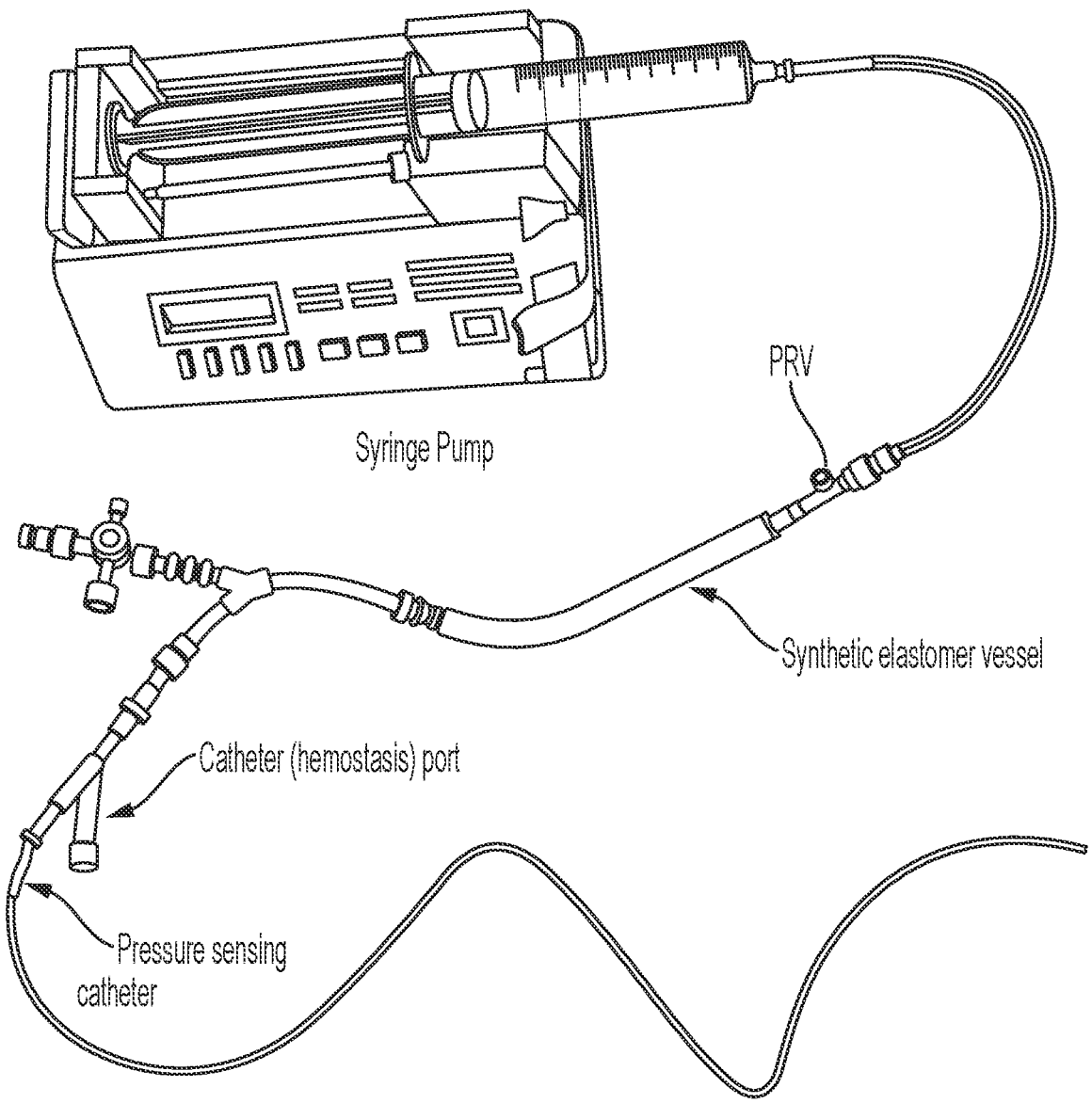
FIG. 5 shows components of a PRV benchtop testing apparatus. A 60 cc syringe is loaded in a syringe pump and connected to a tubing circuit, which includes a 3D-printed vessel. The vessel is cannulated at the distal end and attached to a hemostasis port to allow catheterization of the vessel with a pressure-sensing catheter.
Figure 6:
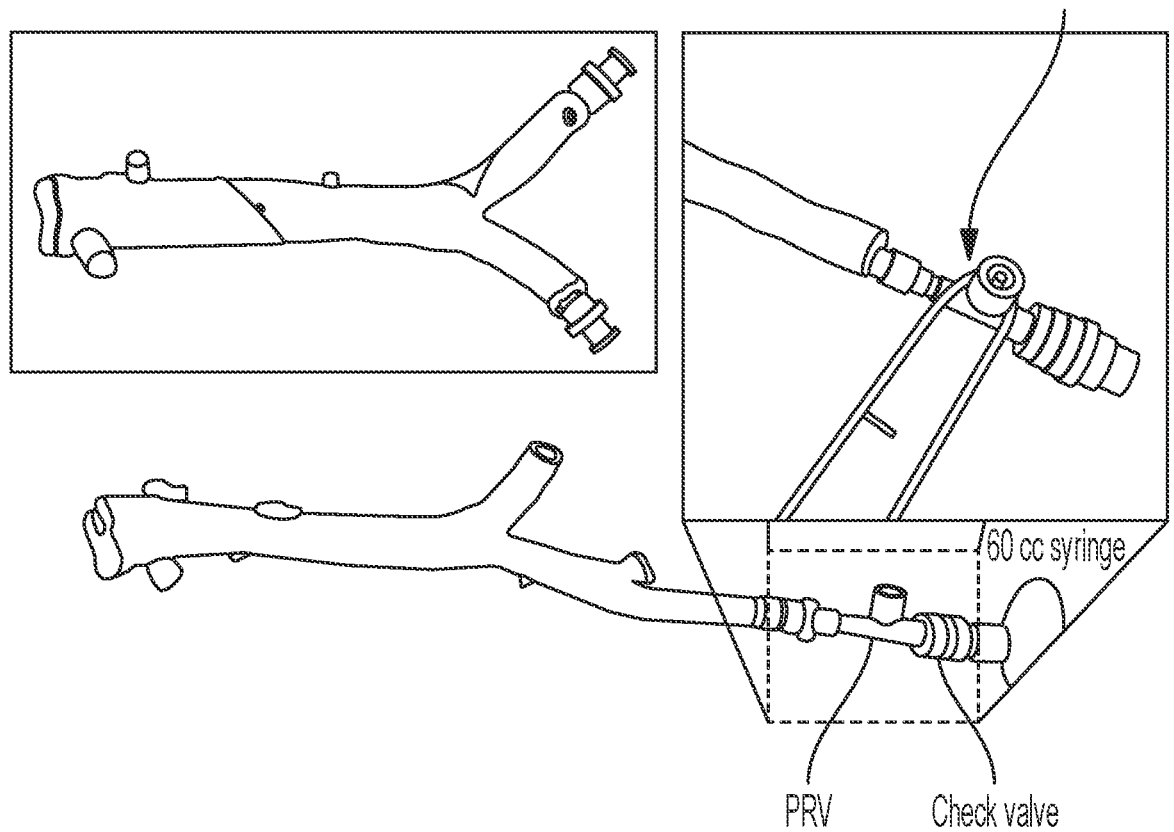
FIG. 6 shows a processed human AI graft including figure-of-eight mattress ligations, with barbed Luer attachments used to cannulate both the iliac branches for connection to PRV and catheter access port (top left panel); a processed human AI graft depicted in a configuration to be used in clinical processing, with a PRV, a check valve, and a 60 cc syringe attached at an iliac and clamped at proximal aortic end (where the top iliac artery would be simply ligated without a barb, however) (bottom panel); and an expanded view of the PRV and other components used in the assembly (top right panel).

The present invention provides a reliable and accurate diameter measurement for an AI graft under a pressure, for example, similar to physiological arterial pressure permitting a more precise and accurate match with a patient's aorta measurement obtained from MRI or CT. In particular, the AI grafts of present invention are provided with measured pressurized diameters, for example, pressurized inner and/or outer diameters.

In surgery to remove an infected previously implanted graft from a patient, the patient's aorta is typically cross clamped to stop blood flow before removing it. The surgeon knows the patient's aorta diameter, from pre-operative imaging, and would choose an AI graft having the best size match with the patient's aorta. The problem is that AI grafts from different donors in general have flaccid (or unpressurized) diameters significantly different from their corresponding pressurized diameters. The pressurized outer diameters cannot be accurately predicted based on flaccid inner diameters. For example, for donors with an 11 mm flaccid (or unpressurized) inner diameter (ID) aorta, an AI graft from one donor may have a distended (or pressurized) outer diameter (OD) of 15 mm while an AI graft from another donor may have a distended (or pressurized) OD of 21 mm. Thus, there are significant differences in distended (or pressurized) ODs among AI grafts from different donors having the same flaccid (or unpressurized) ID and the pressurized ID/OD cannot be accurately or reliably predicted from the flaccid ID. As soon as the aorta cross clamp is released, this difference in pressurized diameter (e.g., pressurized ID or OD) will be observed. If the difference is too great (e.g., more than 20, 30, 40, 50, 60, 70% different from the patient's aorta diameter), this is called a patient mismatch. Then, the surgeon needs to modify either the graft, the patient's aorta or in the instance of a gross mismatch modify both the patient's aorta and the graft to get the diameters to match more closely to avoid excessive turbulent blood flow. According to the invention, the best way to avoid patent mismatch is to measure and report the pressurized ID or OD of the AI graft when processing it. This is a major advantage of the present invention.

The term "aortoiliac artery (AI) graft" as used herein refers to the portion of aortoiliac artery (AI) isolated from a donor beginning distal to the diaphragm and ending at the iliofemoral junction. The donor may be a mammal, preferably a human. The AI grafts may have different configurations to serve patients with varying pathology and anatomy (FIGS. 10A-F).

The term "processing" as used herein refers to a method of preparing the AI graft by treatment of the isolated AI graft before clinical use. The processing may include dissection, determination of the configurations and/or sizes of the AI graft, disinfection cryopreservation, decellularization or devitalization, preservation and terminal sterilization.

The AI graft may comprise a full aortoiliac artery, an abdominal aorta distal to renal arteries inclusive of iliac arteries to an iliofemoral junction, or an abdominal aorta distal of renal arteries and inclusive of at least 1 cm of an iliac artery. The aortoiliac artery may comprise a distal aorta and iliacs without renal arteries. The aortoiliac graft may comprise an aorta distal of a diaphragm to iliofemoral junction.

The aortoiliac artery graft may comprise an aorta artery and one or two iliac artery. The aortoiliac artery graft may further comprise one or two renal artery. The aortoiliac artery graft may further comprise an iliofemoral junction.

The aortoiliac artery graft may be decellularized. A decellularization process may be performed after cutting of a processed tissue material, for example, an aortoiliac artery graft, without damage to matrix and/or tissue structure of the tissue material and may employ detergents, dodecyl sulphates, endonuclease, and decontaminating agents. The matrix structure may include collagens, hyaluronins, elastins, mucopolysaccharides and proteoglycans, among other components. In another aspect, the processing described herein may also comprise sterilizing the tissue material. Sterilization may involve the use of ionizing radiation, in some examples. In other examples, the absorbed dose of ionizing radiation may be between 8.0 KGy and 50 KGy, between 8.0 KGy and 25 KGy, or between 8.0 KGy and 18 KGy. In some examples, the sterilizing step may include placing a packaged graft on dry ice and irradiating the packaged product. In certain examples, sterilization may be performed at a temperature of between −20° C. and −50° C. The processed tissue material described herein may be sterilized using gamma irradiation, supercritical carbon dioxide, ethylene oxide, or electronic-beam.

The aortoiliac artery graft may be devitalized. A devitalization process may be performed after cutting of the processed tissue material, for example, an aortoiliac artery graft, without damage to matrix and/or tissue structure of the tissue material and may employ detergents, sarcosinates, endonuclease, and decontaminating agents. The matrix structure may include collagens, hyaluronins, elastins, mucopolysaccharides and proteoglycans, among other components. In another aspect, the processing described herein may also comprise sterilizing the tissue material. Sterilization may involve the use of ionizing radiation, in some examples. In other examples, the absorbed dose of ionizing radiation may be between 8.0 KGy and 50 KGy, between 8.0 KGy and 25 KGy, or between 8.0 KGy and 18 KGy. In some examples, the sterilizing step may include placing a packaged graft on dry ice and irradiating the packaged product. In certain examples, sterilization may be performed at a temperature of between −20° C. and −50° C. The processed tissue material described herein may be sterilized using gamma irradiation, supercritical carbon dioxide, ethylene oxide, or electronic-beam.

The aortoiliac artery graft may be plasticized using a solution comprising glycerol at a concentration in the range of, for example, about 20-80%, 15-75%, 30-70%, 20-60%, 35-60%, 40-60%, 45-60% or 50-55% by volume. The glycerol concentration may be about 55% by volume. The plasticization processing described herein may further comprise treating the tissue material, for example, an aortoiliac artery graft, with a water-replacing agent. The water replacing agent may comprise one or more selected from the group consisting of glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, meso-erythritol, adipic acid, proline, hydroxyproline, polyethylene glycol, alcohol, and lipids. The processing described herein may further comprise plasticizing the tissue material according to the teachings of one or more of U.S. Pat. Nos. 6,293,970, 6,569,200, 6,544,289, 7,063,726, or U.S. Patent Application Publication Nos. 2010/0030340, 2014/0180437, 2011/0015757, and 2013/0218294, each of which is incorporated herein by reference by its entirety.

A package is provided. The package comprises an aortoiliac artery graft and a first record. The first record may provide a measured pressurized diameter of the aortoiliac artery graft. The measured pressurized diameter may be determined ex vivo during processing under a pressure, for example, similar to an arterial pressure permitting a more precise and accurate match with a patient's aorta. The measured pressurized diameter may be a measured pressurized outer diameter (also known as a distended outer diameter) of the aortoiliac artery graft and may be determined using a syringe with a 130-mmHg pressure relief valve attached and methods of measurement common in the field. The diameter may be measured at the most distal portion of the aorta (FIG. 10). The measured pressurized diameter may be a measured pressurized inner diameter of the aortoiliac artery graft and may be determined using ultrasound. The first record may be a package marking, label or package insert (FIG. 9).

The package may further comprise a second record. The second record may provide a measured unpressurized diameter of the aortoiliac artery graft (FIG. 10). The unpressurized diameter may be determined ex vivo during processing. The measured unpressurized diameter may be a measured unpressurized outer diameter of the aortoiliac artery graft. The measured unpressurized diameter may be a measured unpressurized inner diameter of the aortoiliac artery graft. The measured unpressurized inner diameter (also known as flaccid inner diameter) may be determined by using Hegar dilator. Additionally, the outer unpressurized diameter may be obtained while the Hegar dilator is in place using common measurement means in the field. The second record may be a package marking, label or package insert.

The applied pressure may be caused by liquid, gas or mechanical pressure. In some embodiments, liquid pressure such as hydrostatic pressure is preferred. The applied pressure may be in a range of 70-170 mmHg, 100-160 mmHg, 110-150 mmHg, 120-140 mmHg, 125-135 mmHg or around 130 mmHg.

A method of processing an aortoiliac artery graft is provided. The processing method comprises subjecting an aortoiliac artery to a physiological pressure ex vivo during processing, and determining a measured pressurized diameter of the aortoiliac artery under the physiological pressure. As a result, a processed aortoiliac artery graft pressurized diameter is obtained. The pressure may be controlled by using a pressure relief valve or a calibrated syringe. The measured pressurized diameter may be determined by using a tool selected from the group consisting of, but not limited to, a ruler, a caliper, an umbilical tape, a laser micrometer and ultrasound. The pressurized diameter may be a measured pressurized outer diameter of the aortoiliac artery. The pressurized diameter may be a measured pressurized inner diameter of the aortoiliac artery.

The processing method may further comprise determining a measured unpressurized diameter of the aortoiliac artery. The measured unpressurized diameter may be a measured unpressurized outer diameter of the aortoiliac artery. The measured unpressurized diameter may be a measured unpressurized inner diameter of the aortoiliac artery. The measured unpressurized diameter may be determined by using a tool selected from the group consisting of, but not limited to, a ruler, a caliper, an umbilical tape, a laser micrometer and ultrasound.

The processing method may further comprise isolating the aortoiliac artery from a donor. The donor may be a mammal, preferably a human.

The processing method may further comprise dissection, disinfection, cryopreservation, decellularization, devitalization, plasticization, packaging and/or terminal sterilization in addition to pressurizing the artery, measuring the ID/OD and subsequently releasing the pressure from the aortoiliac artery.

For each processing method, a resulting processed aortoiliac artery graft is provided.

A method of treating abdominal aortic aneurysm, infected aortoiliac endograft or a traumatically damaged abdominal aorta or iliac arteries in a patient is provided. The treatment method comprises anastomosing a processed aortoiliac artery graft with an aorta of the patient on the proximal end and the iliac or femoral arteries on the distal end. A measured pressurized diameter of the processed aortoiliac artery graft may be determined ex vivo under a pressure.

The treatment method may further comprise matching the measured pressurized diameter of the processed aortoiliac artery graft with a diameter measurement of the aorta of the patient before the anastomosing step. The diameter measurement of the aorta of the patient may be obtained by a CT scan, for example, a CT contrast scan.

According to the treatment method of the present invention, the measured pressurized diameter of the processed aortoiliac artery graft may be within 80-120%, 85-115%, 90-110%, 95-105%, 97-103% or 99-101% of the diameter measurement of the aorta of the patient. In one embodiment, the measured pressurized diameter of the processed aortoiliac artery graft is a measured pressurized outer diameter of the processed aortoiliac artery graft, the diameter measurement of the aorta is an inner diameter measurement of the aorta, and the measured pressurized outer diameter of the processed aortoiliac artery graft is within 80-120%, 85-115%, 90-110%, 95-105%, 97-103% or 99-101% of the inner diameter measurement of the aorta.

The term "about" as used herein when referring to a measurable value such as an amount, a percentage, and the like, is meant to encompass variations of ±20% or ±10%, ±5%, ±1%, or ±0.1% from the specified value, as such variations are appropriate.

Example 1. Diameter Measurements of Aortoiliac Artery Grafts

The flaccid inner diameters (ID) and distended outer diameters (OD) of 16 clinical aortoiliac artery (AI) grafts (Table 1) and 49 developmental aortoiliac artery (AI) grafts (Table 2) were determined. The AI grafts were prepared for measurement by cleaning of adipose tissue. All arteries were ligated with prolene. The aorta was clamped. A cannula was ligated to one of the iliac arteries. A calibrated Medtronic 125 mm Hg syringe was filled with isotonic saline and the graft inflated for the OD measurement, which was taken with a ruler. The distended OD was obtained using the calibrated Medtronic 125 mm Hg syringe and inflating to a target pressure of 125 mm Hg. The ligations were removed and the flaccid ID was obtained using Hegar dilators. The mean and standard (std) are of the percent change column.

TABLE 1

Clinical Grafts

| Code | Flaccid ID (mm) | Dist OD (mm) | % | Mean | Std |
|---|---|---|---|---|---|
| DAI1016 | 10 | 16 | 38% | | |
| DAI1016 | 10 | 16 | 38% | | |
| AI1017 | 10 | 17 | 41% | | |
| AI1020 | 10 | 20 | 50% | 42% | 6% |
| DAI1115 | 11 | 15 | 27% | | |
| DAI1116 | 11 | 16 | 31% | | |
| DAI1116 | 11 | 16 | 31% | | |
| DAI1117 | 11 | 17 | 35% | | |
| AI1117 | 11 | 17 | 35% | | |
| DAI1117 | 11 | 17 | 35% | | |
| DAI1118 | 11 | 18 | 39% | | |
| AI1118 | 11 | 18 | 39% | | |
| AI1121 | 11 | 21 | 48% | 36% | 6% |
| ABA1218 | 12 | 18 | 33% | | |
| AI1221 | 12 | 21 | 43% | | |
| AI1221 | 12 | 21 | 43% | 40% | 5% |

TABLE 2

Developmental Grafts

| Flaccid ID (mm) | Dist OD (mm) | % | Mean | Std |
|---|---|---|---|---|
| 10 | 14 | 29% | | |
| 10 | 15 | 33% | | |
| 10 | 16 | 38% | | |
| 10 | 16 | 38% | | |
| 10 | 18 | 44% | 36% | 6% |
| 11 | 13 | 15% | | |
| 11 | 15 | 27% | | |
| 11 | 16 | 31% | | |
| 11 | 16 | 31% | | |
| 11 | 16 | 31% | | |
| 11 | 17 | 35% | | |
| 11 | 17 | 35% | | |
| 11 | 17 | 35% | | |
| 11 | 18 | 39% | | |
| 11 | 18 | 39% | | |
| 11 | 19 | 42% | 33% | 7% |
| 12 | 16 | 25% | | |
| 12 | 17 | 29% | | |
| 12 | 17 | 29% | | |
| 12 | 18 | 33% | | |
| 12 | 18 | 33% | | |
| 12 | 18 | 33% | | |
| 12 | 18 | 33% | | |
| 12 | 18 | 33% | | |
| 12 | 18 | 33% | | |
| 12 | 19 | 37% | | |
| 12 | 19 | 37% | | |
| 12 | 19 | 37% | | |
| 12 | 20 | 40% | | |
| 12 | 20 | 40% | | |
| 12 | 21 | 43% | 34% | 4% |
| 13 | 15 | 13% | | |
| 13 | 16 | 19% | | |
| 13 | 16 | 19% | | |
| 13 | 18 | 28% | | |
| 13 | 19 | 32% | | |
| 13 | 19 | 32% | | |
| 13 | 22 | 41% | | |
| 13 | 22 | 41% | 28% | 10% |
| 14 | 18 | 22% | | |

TABLE 2-continued

Developmental Grafts

| Flaccid ID (mm) | Dist OD (mm) | % | Mean | Std |
|---|---|---|---|---|
| 14 | 18 | 22% | | |
| 14 | 20 | 30% | | |
| 14 | 20 | 30% | | |
| 14 | 21 | 33% | | |
| 14 | 22 | 36% | 29% | 6% |
| 16 | 21 | 24% | | |
| 16 | 22 | 27% | | |
| 17 | 22 | 23% | 25% | 2% |

Example 2. Additional Embodiments

Additional embodiments according to the present invention are shown in FIGS. 1-8.

Some definitions are set forth below:

1. BacT/Alert (BTA) bottles: Bottles used to collect and incubate microbial (Aerobic and Anaerobic) samples for testing in the Bac-T-Alert system.

2. Cold pack: Frozen block/ice substitute used to maintain the dissection solution temperature within a range of 1-10° C. during the processing procedure.

3. Microbiological Samples: Refers to the Processing Representative sample (PRS) and Representative Sample (RS).

4. Processing Filter (PF): A 0.2 micron filter used to filter the last rinse solution. The filter is plated and used for microbial testing.

5. Processing Representative Sample (PRS): A 1 cm×1 cm sample piece of tissue co-processed with the tissue intended for transplant. It is considered "processing" as it is never exposed to disinfection solution.

6. Representative Sample (RS): A 1 cm×1 cm sample piece of tissue co-processed with the tissue intended for transplant through final packaging.

7. CV disinfection solution: Combination of antibiotics and RPMI used to disinfect CV tissue. Refer to MP-10-021 for preparation procedure.

8. Meropenem: The diluted 2.5 ml dose of Meropenem prepared according to instructions in MP-10-021.

9. Eraxis: The diluted 2.5 ml dose of Eraxis (Anidulafugin) prepared according to instructions in MP-10-021.

10. Suture Ligature: A strand of suture material attached to a needle to ligate a vessel, duct or other structure. The needle is passed through the structure, or adjacent tissue first to anchor the suture, then tied around the structure.

11. F8: Refers to a specific type of suture ligature technique, the figure-of-eight mattress ligature 12. Major arterial branches: Arteries that depart from the aorta to supply blood to major organs and or structures (e.g., celiac, superior and inferior mesenteric, and renal).

13. Minor arterial branches: All other branches that are not considered by definition as major arterial branches.

14. TOD: Time of Death.

For aortoiliac artery graft sizing, the dimensions of the graft are measured as follows:

1. Aorta flaccid diameter (AFD): Measure in mm, inner diameter (ID) of the flaccid aorta with a Hegar dilator where the OD measurement was obtained so they are relatable. To measure, wet the dilator and slide it into the aorta. The appropriate dimension sizer should slide into the artery without any pressure inside the vessel and without leaving gaps or dilation of the arterial wall. This technique is analogous to that used to obtain the annulus measurement for a heart valve.

2. Aorta length (AL): Measure, in cm, the flaccid aorta from the proximal end of the aorta to saddle region of the common R&L iliac arteries.

3. Iliac arteries, right (RIA) and left (LIA): Measure, in cm, flaccid iliac arteries from the origin at the aorta to distal end of the right and left iliac arteries.

4. Major arterial branches (celiac trunk, superior mesenteric artery and renal arteries): Measure in cm, flaccid conditions. Minimum acceptable length is ≥0.5 cm when measured from the aorta distally to the end of the artery.

5. Total Flaccid Length (TFL): Measure in cm, under flaccid conditions, from the proximal end of the aorta to the distal end of the shortest iliac artery.

Figure 7:
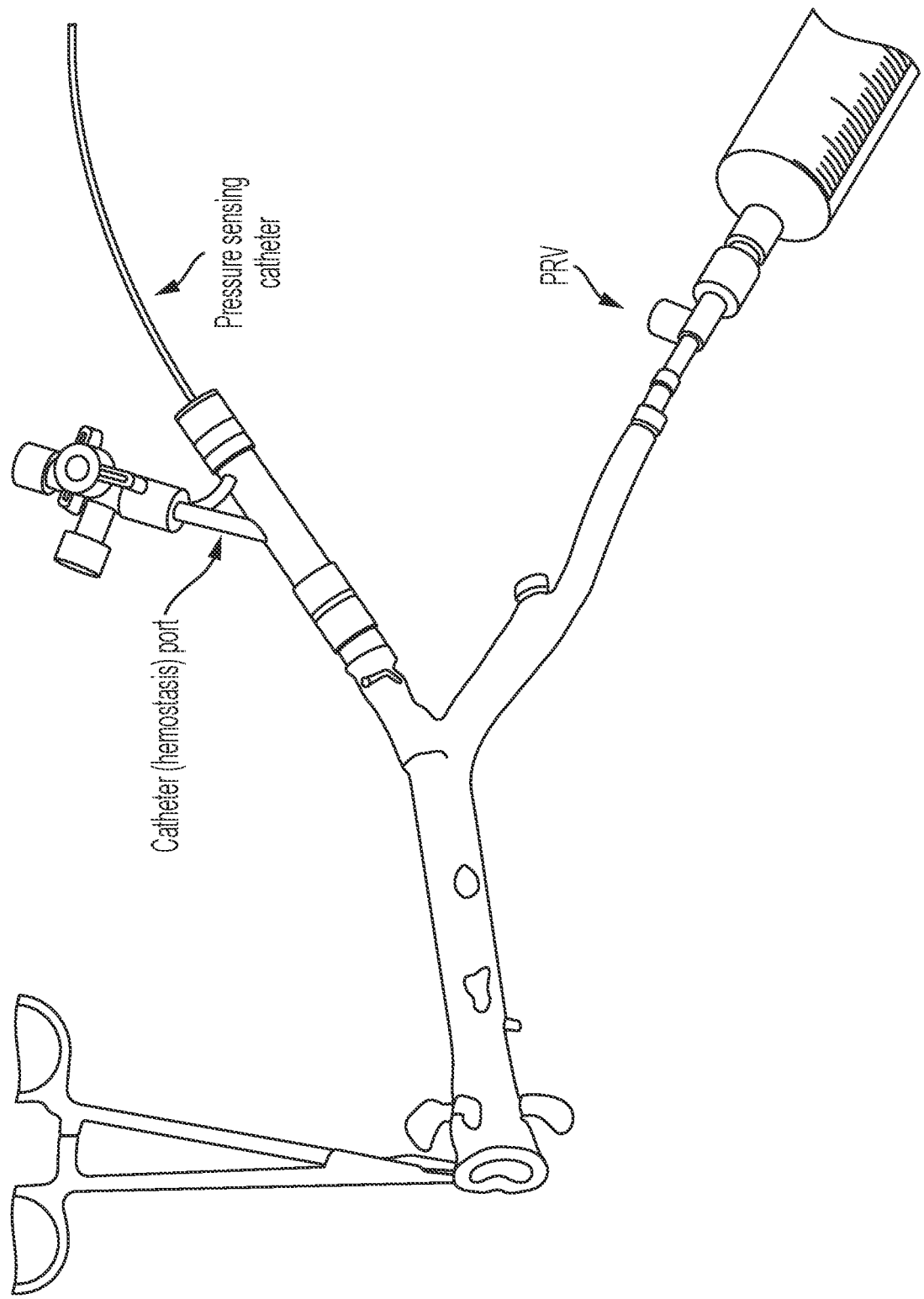
FIG. 7 shows components of a setup for a validation section of testing. An AI graft depicted in the configuration to be used in clinical processing, with PRV, check valve, and 60 cc syringe attached at an iliac and clamped at proximal aortic end. The other iliac artery will be used to advance a pressure-sensing catheter into the lumen of the graft.
Figure 8:
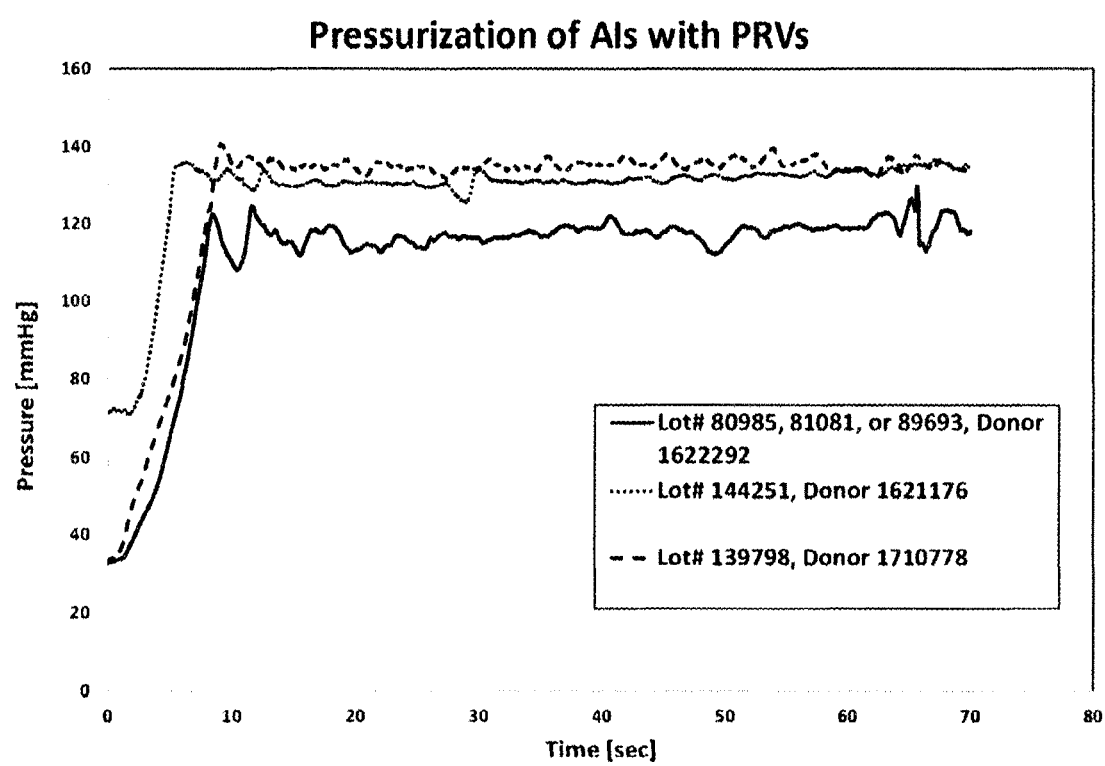
FIG. 8 shows pressurization of AIs with PRVs with a plot of pressure vs. time generated from pressurization of three different AIs with PRVs from the indicated lots. Data were recorded using a pressure-sensing catheter and LabView software. The pressures in the 60-second period following valve opening (the first pressure peak) were analyzed to see if the PRV could enable maintenance of stable pressure.
Figure 9B:
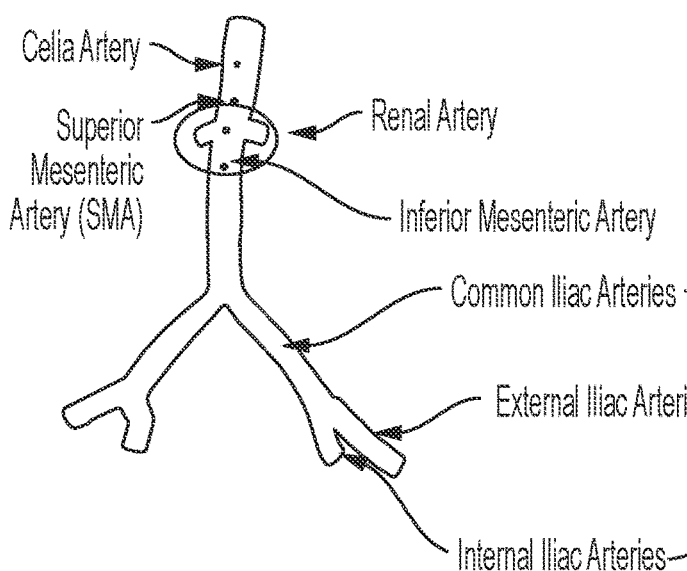
Figure 9B:
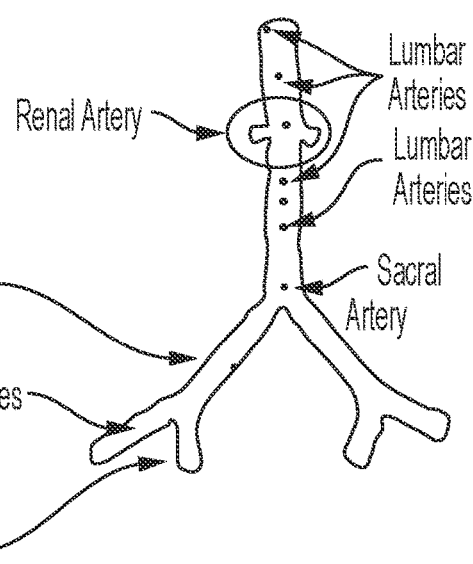
Figure 9C:
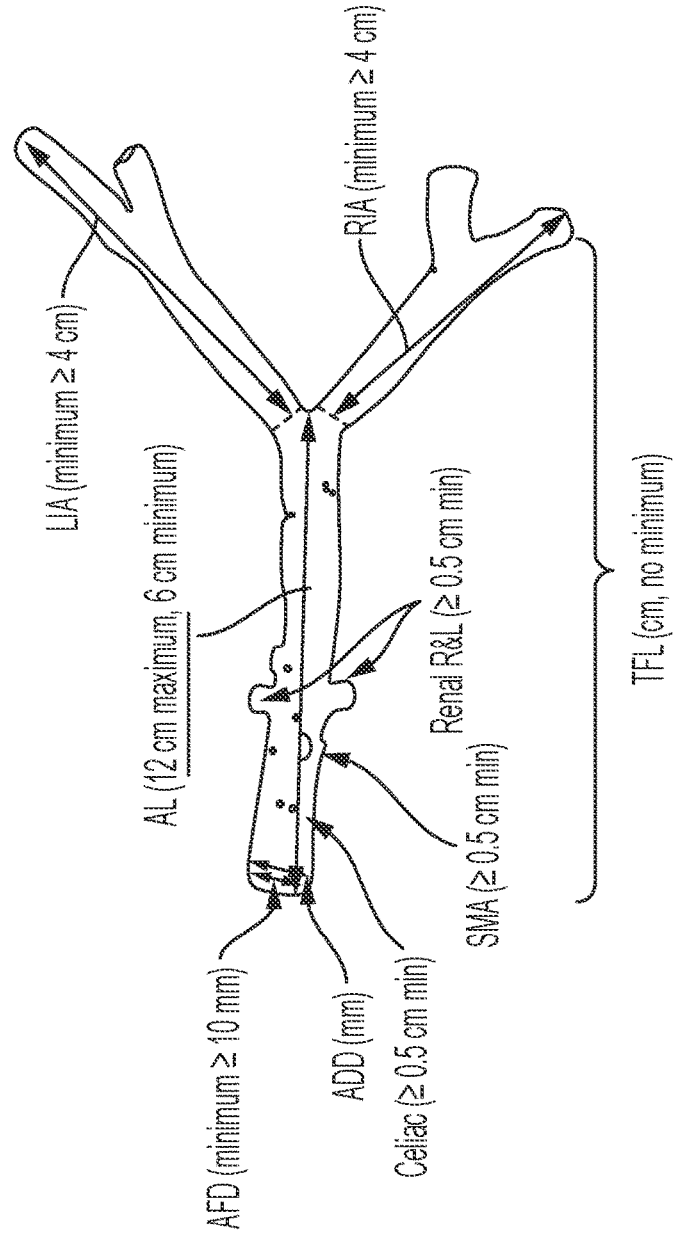
Figure 9D:
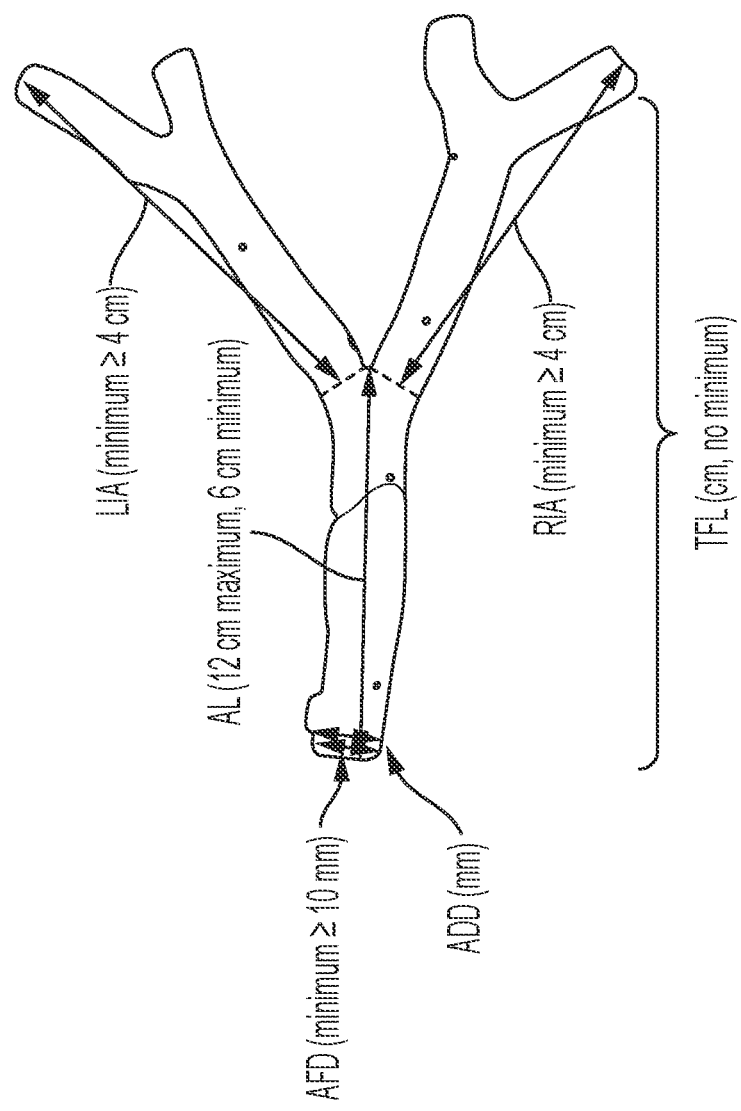
Figure 9E:
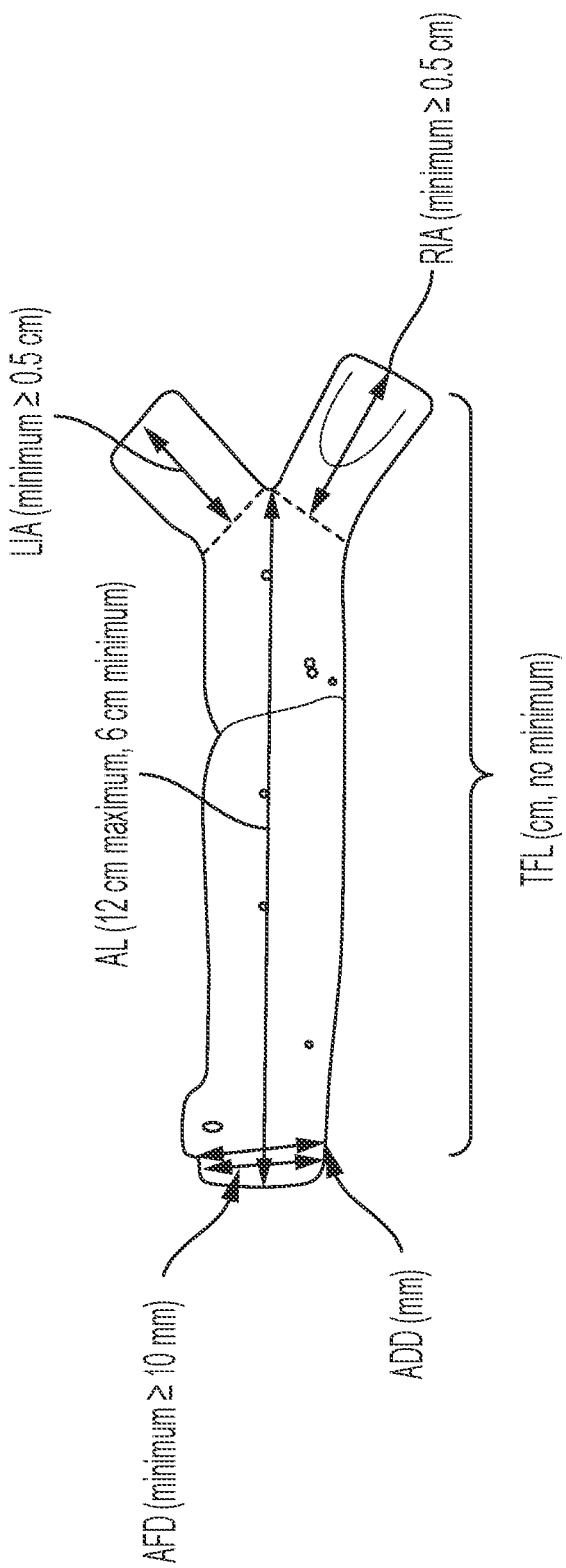
Figure 9F:
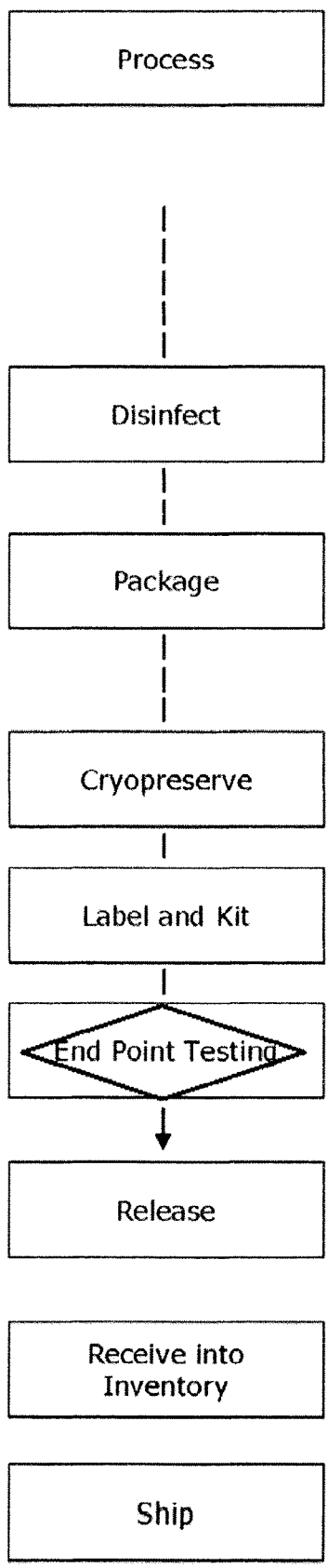
Figure 10B:

The setup with the PRV is similar in FIGS. 7 and 8. The pressurized ID is obtained by inflating vessel with normal saline. A high frequency (7-10-MHz) ultrasound transducer is used, which allows higher spatial resolution to obtain a highly accurate+/−3% pressurized ID. B-mode US is used because it provides high resolution image of the lumen of the AI. In one example, cross-sectional images are obtained perpendicular to the aorta at the most proximal portion of the aorta, the line drawing tool is selected, a line is drawn connecting the opposing lumen walls and the ID is displayed on the screen. This is repeated two more times, and then the three lengths are averaged and reported.

Example 3. Decellularization Processing of Arteries

The main goal of this study was to further optimize arterial decellularization process to produce more robust decellularization while maintaining matrix integrity of arteria grafts. One objective was to reduce the preservation step's glycerol concentration from 77% glycerol and assess the degree to which various reduced glycerol concentrations (15%, 30%, 45%, 60%) protect the matrix from either compaction or damage during processing, freezing, and gamma irradiation.

An investigation of various glycerol concentrations was performed because higher concentrations increase intraluminal pressure generation (and therefore require limiting flow rate to avoid damage from over pressurization), but lower concentrations contain too much water, which could result in freezing artifacts and/or free radical-induced damage from irradiation. Consequently, the study intended to identify a glycerol concentration that provided a balance between increasing flow rate to improve the robustness of decellularization and maintaining matrix integrity during processing, freezing, and gamma irradiation.

The residual DNA acceptance criterion was met and decellularization was achieved for all treatment groups. Additionally, differential scanning calorimetry did not indicate significant matrix damage nor any differences between glycerol concentrations. Histological assessment showed that 15% glycerol did not protect the arterial matrix, as an unacceptable number of gaps between the collagen and elastin in the extracellular matrix were visible. It was also determined that 30% glycerol was borderline acceptable for matrix integrity based upon histological review. Both 45% and 60% glycerol protected matrix integrity during freezing and gamma irradiation without compaction. Finally, 77% glycerol produced unacceptable matrix compaction that could potentially hinder length and compaction recovery upon dilution. Mercury intrusion and hemocompatibility testing did not demonstrate statistically significant differences between groups.

Overall, the data suggest that reducing glycerol concentration while increasing process flow rate is a viable approach to improving robustness of decellularization for arterial tissues. Results suggest the acceptable range of glycerol concentrations for preserving matrix integrity range from 30%-60%, with 30% still potentially questionable in that regard.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A package comprising an aortoiliac artery graft and a first record, wherein the first record provides a measured pressurized diameter of the aortoiliac artery graft, and wherein the measured pressurized diameter has been determined ex vivo under a pressure.

2. The package of claim 1, wherein the measured pressurized diameter is a measured pressurized outer diameter of the aortoiliac artery graft.

3. The package of claim 1, wherein the measured pressurized diameter is a measured pressurized inner diameter of the aortoiliac artery graft.

4. The package of claim 1, further comprising a second record, wherein the second record provides a measured unpressurized diameter of the aortoiliac artery graft, wherein the unpressurized diameter has been determined ex vivo during processing.

5. The package of claim 4, wherein the measured unpressurized diameter is a measured unpressurized outer diameter of the aortoiliac artery graft.

6. The package of claim 4, wherein the measured unpressurized diameter is a measured unpressurized inner diameter of the aortoiliac artery graft.

7. The package of claim 1, wherein the aortoiliac artery graft comprises a full aortoiliac artery, an abdominal aorta distal to renal arteries inclusive of iliac arteries to an iliofemoral junction, or an abdominal aorta distal of renal arteries and inclusive of at least 1 cm of an iliac artery.

8. The package of claim 1, wherein the aortoiliac artery comprises a distal aorta and iliacs without renal arteries.

9. The package of claim 1, wherein the aortoiliac graft comprises an aorta distal of a diaphragm to iliofemoral junction.

10. The package of claim 1, wherein the aortoiliac artery graft comprises an aorta artery and one iliac artery.

11. The package of claim 1, wherein the aortoiliac artery graft comprises an aorta artery and two iliac arteries.

12. A method of processing an aortoiliac artery graft, comprising
    (a) subjecting an aortoiliac artery to a pressure ex vivo during processing, and
    (b) determining a measured pressurized diameter of the aortoiliac artery under the pressure, whereby a processed aortoiliac artery graft is obtained.

13. The method of claim 12, wherein the pressure is controlled by using a pressure relief valve or a calibrated syringe.

14. The method of claim 13, wherein the measured pressurized diameter is determined by using a tool selected from the group consisting of a ruler, a caliper, an umbilical tape, a laser micrometer and ultrasound.

15. The method of claim 12, wherein the pressurized diameter is a measured pressurized outer diameter of the aortoiliac artery.

16. The method of claim 12, wherein the pressurized diameter is a measured pressurized inner diameter of the aortoiliac artery.

17. A processed aortoiliac artery graft prepared according to the method of claim 12.

18. A method of treating abdominal aortic aneurysm, infected aortoiliac endograft or a traumatically damaged abdominal aorta or an iliac artery in a patient, comprising anastomosing a processed aortoiliac artery graft with an aorta of the patient on the proximal end and the iliac or femoral arteries on the distal end, wherein a measured pressurized diameter of the processed aortoiliac artery graft has been determined ex vivo under a pressure.

19. The method of claim 18, further comprising matching the measured pressurized diameter of the processed aortoiliac artery graft with a diameter measurement of the aorta of the patient before the anastomosing step.

20. The method of claim 18, wherein the measured pressurized diameter of the processed aortoiliac artery graft is within 90-110% of the diameter measurement of the aorta of the patient.

* * * * *